US010834908B2

(12) United States Patent
Holmberg

(10) Patent No.: US 10,834,908 B2
(45) Date of Patent: Nov. 17, 2020

(54) MODEL ANIMAL FOR FIBROSIS

(71) Applicant: InfiCure Bio AB, Umeå (SE)

(72) Inventor: Dan Holmberg, Umeå (SE)

(73) Assignee: INFICURE BIO AB, Umeå (SE)

( * ) Notice: Subject to any disclaimer, the term of this patent is extended or adjusted under 35 U.S.C. 154(b) by 343 days.

(21) Appl. No.: 15/917,511

(22) Filed: Mar. 9, 2018

(65) Prior Publication Data

US 2018/0310535 A1 Nov. 1, 2018

(30) Foreign Application Priority Data

Apr. 26, 2017 (EP) ..................................... 17168167

(51) Int. Cl.
| | |
|---|---|
| C12N 5/00 | (2006.01) |
| A01K 67/027 | (2006.01) |
| A61K 49/00 | (2006.01) |
| A61P 29/00 | (2006.01) |
| C12N 9/22 | (2006.01) |
| C07K 14/725 | (2006.01) |

(52) U.S. Cl.
CPC ...... *A01K 67/0275* (2013.01); *A61K 49/0008* (2013.01); *A61P 29/00* (2018.01); *C07K 14/7051* (2013.01); *C12N 9/22* (2013.01); *A01K 2217/052* (2013.01); *A01K 2217/15* (2013.01); *A01K 2227/105* (2013.01); *A01K 2267/0368* (2013.01)

(58) Field of Classification Search
CPC .......... A01K 67/0275; A01K 2227/105; A01K 2217/15
See application file for complete search history.

(56) References Cited

U.S. PATENT DOCUMENTS

| | | | | |
|---|---|---|---|---|
| 2009/0203629 A1* | 8/2009 | Holsinger | ............... | A61P 17/00 514/1.1 |
| 2011/0302665 A1* | 12/2011 | Kirak | ................... | C12N 15/877 800/8 |

OTHER PUBLICATIONS

Naito et al. J Reprod Fert 113:137-143, 1998. (Year: 1998).*
Raina et al. Gene 96-100, 2015 (Year: 2015).*
Dolatshad et al. Mammalian Genome 26:598-608, 2015 (Year: 2015).*
Sellers et al. Veterinary Pathology 49(1):32-43, 2012 (Year: 2012).*
Doetschman et al. Methods Mole Biol 530:423-433, 2009 (Year: 2009).*
Skold et al. J Immunol 165:168-174, 2000 (Year: 2000).*
Kouskoff et al. J of Immunol Methods 180:273-280, 1995 (Year: 1995).*
Fransén-Pettersson et al., "A New Mouse Model That Spontaneously Develops Chronic Liver Inflammation and Fibrosis", PLOS ONE, 2016, DOI:10.1371/journal.pone.0159850.
Bandyopadhyay et al., "NKT cell subsets as key participants in liver physiology and pathology"; Cellular & Molecular Immunology (2016) 13: 337-346.
Bendelac et al., "The Biology of NKT Cells"; Annu. Rev. Immunol (2007) 25: 297-336.
Bendelac, Positive Selection of Mouse NK1$^+$ T Cells by CD1-expressing Cortical Thymocytes; Brief Definitive Report ; Dec. 1995; 182: 2019-2096.
Chuang et al.,"Animal models of primary biliary cirrhosis"; Clin Liver Dis. May 2008; 12(2): 333-ix.
De Lalla et al., "Production of Profibrotic Cytokines by Invariant NKT Cells Characterizes Cirrhosis Progression in Chronic Viral Hepatitis"; The Journal of Immunology, 2004; 173: 1417-1425.
Duarte et al., "Prevention of Diabetes in Nonobese Diabetic Mice Medicated by CD1d-Restricted Nonclassical NKT Cells"; J Immunol, 2004; 173: 3112-3118.
Duffield et al.,"Host Responses in Tissue Repair and Fibrosis"; Annu Rev Pathol.,Jan. 24, 2013; 24; 8: 241-276.
Godfrey et al.,"Raising the NKT cell family"; Nature Immunology; Mar. 2010; 11(3):197-206.
Iredale et al.,"Models of liver fibrosis: exploring the dynamic nature of inflammation and repair in a solid organ"; The Journal of Clinical Investigation; Mar. 2007; 117(3):539-548.
Ishikaws et al.,"CD1d-restricted natural killer T cells contribute to hepatic inflammation and fibrogenesis in mice"; Journal of Hepatology ,2011; 54: 1195-1204.
Kadri et al.,"CD4$^+$ Type II NKT Cells Mediate ICOS and Programmed Death-1-Dependent Regulation of Type 1 Diabetes"; J Immunol, 2012; 188: 3138-3149.
Kumar et al., "Different subsets of natural killer T cells may vary in their roles in health and disease"; John Wiley & Sons Ltd, Immunology, 2004; 142: 321-336.
Liberal et al.,"Regulatory T Cells: Mechanisms of Suppression and Impairment in Autoimmune Liver Disease"; International Union of Biochemistry and Molecular Biology, Feb. 2015; 67(2): 88-97.
Mehal et al.,"Scraping fibrosis: Expressway to the core of fibrosis"; Nat Med. , May 2011; 17(5): 552-553.
Park et al.,"Diverse Roles of Invariant Natural Killer T Cells in Liver Injury and Fibrosis Induced by Carbon Tetrachloride"; Hepatology, May 2009 ; 49(5): 1683-1694.
Poon et al.,"Apoptotic cell clearance: basic biology and therapeutic potential";Nature Reviews Immunology, Mar. 2014; 14: 166-180.
Takeda et al.,"Critical contribution of liver natural killer T cells to a murine model of hepatitis"; PNAS, May 9, 2000; 97 (10): 5498-5503.
Wang et al.,"Breach of tolerance: primary biliary cirrhosis"; Semin Liver Dis 2014;34:297-317.

(Continued)

*Primary Examiner* — Marcia S Noble
(74) *Attorney, Agent, or Firm* — James S. Keddie; Bozicevic, Field & Francis LLP

(57) ABSTRACT

Disclosed is a non-human animal comprising a genetic construct expressing TCRα and TCRβ genes and wherein the animal comprises a null-mutated Rag-2 locus. Described herein is also a NOD.Rag2$^{-/-}$ mouse expressing a transgenic α,β T cell receptor. The animals spontaneously develop chronic inflammation and fibrosis, and are useful as animal models of fibrotic disease.

10 Claims, 5 Drawing Sheets

(56) References Cited

OTHER PUBLICATIONS

Pellicoro et al., "Liver fibrosis and repair: immune regulation of wound healing in a solid organ"; Nature reviews, Immunology; Mar. 2014;vol. 4:p. 181-194.

* cited by examiner

A

B

Liver weight in grams

Body weight in grams

LW/BW ratio

Scale bars are 500 μm in the overview images
(left) and 100 μm in the enlarged images (right)

A Total spleen leukocytes

B Total liver leukocytes

MODEL ANIMAL FOR FIBROSIS

CROSS-REFERENCE TO RELATED APPLICATIONS

This application claims the benefit of European Application No. 17168167.9, filed on Apr. 26, 2017, which application is incorporated by reference herein.

FIELD OF THE INVENTION

The present invention relates to non-human model animals of fibrosis, and to uses thereof.

BACKGROUND

Chronic hepatic disease and the associated development of hepatic fibrosis constitute a major health problem worldwide. Despite increasing understanding of the mechanisms controlling the transition of an immunological response to hepatic stress and injury into the accumulation of extracellular matrix and fibrosis, no efficient therapies aimed at the fibrotic process are currently available.

The formation of the extracellular matrix is critical during wound healing, but excessive production, as seen in both local and systemic chronic inflammatory conditions, can lead to fibrosis and be detrimental to tissue function (Duffield et al. Annu Rev Pathol 8:241, 2013). Fibrosis can affect almost any organ or tissue and is manifested in many conditions, such as pulmonary fibrosis, renal fibrosis and hepatic cirrhosis. Fibrosis represents a large therapeutic area because an estimated >45% of all natural deaths in the western world are caused by an underlying fibrotic condition (Mehal et al. Nat. Med. 17:552, 2011).

For the development of effective methods and agents for treating hepatic fibrosis, it is essential to elucidate the pathological condition of the disease. While intense research has improved our understanding of fibrotic conditions, there has been no approved drug specifically targeting fibrosis until recently (Pellicoro et al. Nat Rev Immunol 14:181, 2014). A major impediment to reaching a better understanding of the molecular mechanisms of the development of fibrosis and to developing efficient anti-fibrotic drugs is the lack of accurate animal models accurately reflecting the condition in humans.

Many induced animal models of human fibrotic conditions are currently available and constitute important tools for the analysis of different aspects of the disease process. Although these models have been instrumental in identifying a number of key cells, mediators, and processes that are likely to be involved in human fibrosis (Iredale et al. J Clin Invest 117:539, 2007), no current animal model recapitulates all the cardinal manifestations of the human disease, and it has been difficult to translate the results obtained from these models into effective treatments for humans. For instance, in $CCl_4$ treated mice and bile duct ligated mice, which are commonly used as hepatic fibrosis models, the pathological condition does not develop uniformly, making the experiments cumbersome and complicated. Furthermore, in these models the pathological lesions are not always preceded by chronic inflammation. This has made the assessment of treatment efficacy difficult (Pellicoro et al. Nat Rev Immunol 14:181, 2014).

Thus, there remains a need in the art for improved methods and models for the development of treatments for hepatic fibrosis.

SUMMARY OF THE INVENTION

The present invention addresses the above-mentioned drawbacks of prior art and aims to provide new fibrosis model animals useful in the development of a therapies for hepatic fibrosis.

Accordingly, in a first aspect, the invention provides a non-human animal comprising a genetic construct expressing TCRα and TCRβ genes and wherein the animal comprises a null-mutated Rag-2 locus. Advantageously, the animal may spontaneously develop chronic inflammation and fibrosis, making the animal useful as a model animal of fibrosis.

In the following, animals according to the invention are sometimes referred to as "animals of the present invention" or "model animals of the present invention".

The present inventor found that animals of the present invention exhibit pathological findings similar to those of human fibrotic disease, in particular human hepatic fibrosis, and that the animals are useful for screening and evaluation of candidate drugs against fibrosis, such as hepatic fibrosis.

Advantageously, a model animal of the present invention may naturally exhibit symptoms of fibrosis, that is, it may exhibit such symptoms spontaneously, without any particular induction, such as chemical, surgical or dietary induction. Furthermore, animals according to embodiments of the present invention unfailingly develop a pathological condition of hepatic fibrosis of similar severity as that of the human condition, as estimated histologically and biochemically. The animals described herein are the first model animals that exhibit the same course of disease progression as humans.

For example, upon examination of an organ, specifically the liver, of an animal of the present invention, the exhibited the following pathological findings were noted:
  (i) Infiltration of inflammatory cells; and
  (ii) Fibrosis around mainly in the portal regions.

These pathological findings are characteristic of several human conditions of hepatic fibrosis.

Fibrosis model animals described herein differ from conventional hepatic fibrosis animal models in the following:
  (i) hepatic fibrosis of hepatic cells progresses mainly in the portal area and around the central vein, as also observed in the histopathological findings of human hepatic fibrosis;
  (ii) Similar to most human conditions associated with hepatic fibrosis, the fibrotic process is preceded by hepatic inflammation;
  (iii) The fibrotic areas displayed accumulation of activated ASMA+hepatic stellate cells, which is also a characteristic of most human hepatic fibrosis conditions.

Moreover, the present inventor found that animals of the invention are capable of developing dermal and renal fibrosis. Thus, the animals of the present invention may be also useful as model animals of fibrosis of the human skin or kidney.

As mentioned above, in the $CCl_4$ treated mice and bile duct ligated mice which are commonly used as hepatic fibrosis models, the pathological condition does not develop uniformly, which makes the experiments cumbersome and complicated. Furthermore, the pathological lesions are not always preceded by chronic inflammation. This has made the efficacy assessment difficult (Pellicoro et al. Nat Rev Immunol 14:181, 2014). Meanwhile, in the model animals of the present invention, the period leading to the mature pathological condition may be constant. Moreover, its progression may be reversible.

In embodiments of the invention, the animal is a non-human mammal, such as a rodent. For example, the animal may be a mouse. In embodiments, where the animal is a mouse, it may be referred to as the "non-obese diabetic inflammation and fibrosis mouse" (N-IF mouse).

In embodiments, the animal may be, may be based on, or may include genetic characteristics of a non-obese diabetic (NOD) model animal, for example a non-obese diabetic mouse.

In embodiments, the animal may exhibit one or more of hepatic inflammation, hepatic fibrosis, abnormal intrahepatic bile ducts, inflammation or fibrosis of the skin, renal inflammation, and renal fibrosis. The inflammation may be chronic inflammation.

In another aspect, the invention provides a NOD.Rag2$^{-/-}$ mouse expressing a transgenic α,β T cell receptor. Such a mouse is also referred to herein as the N-IF mouse. The present inventor surprisingly found that such a mouse spontaneously develops inflammation and fibrosis of multiple organs, most notably the liver. In embodiments, the N-IF mouse may exhibit one or more of hepatic inflammation, hepatic fibrosis, abnormal intrahepatic bile ducts, inflammation or fibrosis of the skin, renal inflammation, and renal fibrosis. The inflammation may be chronic inflammation.

A model animal according to embodiments of the invention may be obtained by crossing the previously described 24αβNOD mouse strain and the previously described NOD.Rag2$^{-/-}$ mouse strain. Hence, in yet another aspect, the invention provides a method of making a genetically modified mouse comprising the steps of:
a) providing fertilized first and second oocytes from a NOD mouse;
b) i. introducing a first genetic construct comprising cDNA of a TCRα gene into said first oocyte, and ii. introducing a second genetic construct comprising cDNA of a TCRβ gene into said second oocyte;
c) implanting said first and second oocytes in one or more surrogate animals to generate at least to two single transgenic mice;
d) breeding said at least two mice together to generate a double transgenic mouse expressing the TCRα and the TCRβ genes;
e) breeding said double transgenic mouse with a NOD.Rag2$^{-/-}$ mouse to introduce a null-mutated Rag-2 locus into said double transgenic mouse.

The mouse obtained by this method was surprisingly found to spontaneously develop inflammation and fibrosis of multiple organs, most notably the liver, and may thus be useful as a model animal of fibrosis, in particular hepatic fibrosis. Accordingly, in further aspects, the invention provides a model animal of hepatic fibrosis, a model animal of renal fibrosis, and a model animal of skin fibrosis, respectively. In embodiments, the model animal may be a model of fibrosis in two or more of said organs.

As described herein, the present inventor has successfully produced model animals for hepatic fibrosis and fibrosis in the skin and/or kidney and which show similar pathological findings to those of human conditions. By using these model animals, it is possible to efficiently screen for substances for treating or preventing fibrotic disease, and to effectively evaluate the efficacy of medicinal substances.

Thus, the invention provides methods of screening for and/or evaluating agent(s) suitable for prevention or treatment of chronic inflammation or fibrosis.

In one such aspect, the invention provides a method of screening for an agent suitable for prevention or treatment of chronic inflammation and/or fibrosis, comprising the steps of
a) administering a test agent to the animal or mouse described herein, wherein said animal or mouse exhibits inflammation and/or fibrosis in at least one organ,
b) evaluating an ameliorating effect on the inflammation and/or fibrosis in said at least one organ.

In another such aspect, the invention provides a method of evaluating the efficiency of a therapeutic agent for treatment of inflammation or fibrosis, comprising the steps of
a) administering a test agent to the animal or the mouse described herein, wherein said animal or mouse exhibits inflammation and/or fibrosis,
b) evaluating an ameliorating effect on the inflammation and/or fibrosis.

In embodiments, the inflammation and/or fibrosis may be selected from the group consisting of hepatic inflammation, hepatic fibrosis, inflammation or fibrosis of the skin, renal inflammation, and renal fibrosis. The inflammation may be chronic inflammation. An ameliorating effect may be represented by one or more of: reduced fibrosis, reduced inflammation, and return to a normal morphology. In embodiments, an ameliorating effect may alternatively or additionally be represented by a reduction of systemic or local production of pro-inflammatory or pro-fibrotic factors, such as cytokines or chemokines, or other markers of inflammation and/or fibrosis known to persons of skill in the art. Hence, the step b) may comprise determining a level of at least one pro-inflammatory or pro-fibrotic factor or other marker of inflammation and/or fibrosis in a sample obtained from said animal after said step a) of administering, and optionally comparing said level with an initial level of said pro-inflammatory or pro-fibrotic factor(s) or marker(s) determined in an initial sample obtained from said animal prior to said step a) of administering. In embodiments, an ameliorating effect may be represented by a decreased level of hydroxyproline in an organ affected by fibrosis relative to a level of hydroxyproline in said organ prior to said administration, and step b) comprises determining the level of hydroxyproline in an affected organ.

It is noted that the invention relates to all possible combinations of features recited in the claims. The mere fact that certain measures are recited in mutually different dependent claims does not indicate that a combination of these measures cannot be used to advantage.

BRIEF DESCRIPTION OF THE DRAWINGS

The invention will now be described in more detail with reference to the appended drawings.

DETAILED DESCRIPTION

Figure 1:
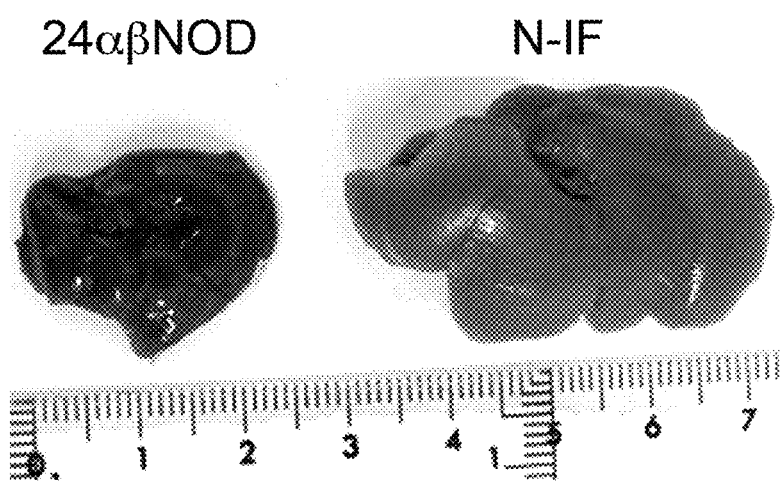
FIG. 1 shows (A) photographs of liver from a fibrotic N-IF mouse according to embodiments of the present invention and a non-fibrotic control mouse, respectively, and (B) graphs showing liver weight, body weight and liver weight/body weight (LW/BW) ratio, respectively, of groups of these mouse strains.
Figure 1:
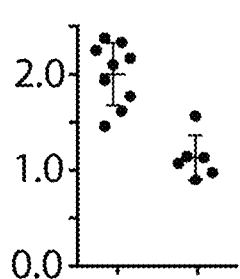
Figure 1:
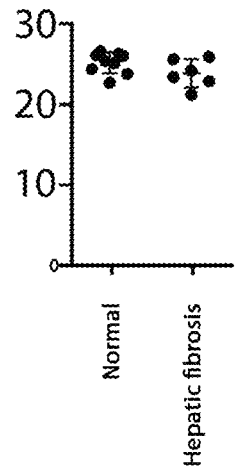
Figure 1:
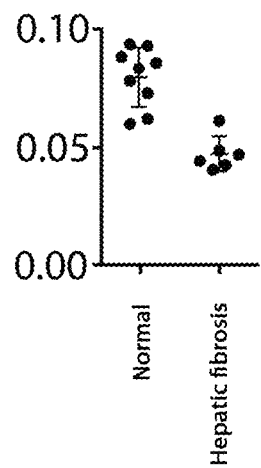

Animals according to embodiments of the present invention were generated by the transgenic expression of a TCRα gene and a TCRβ gene in combination with the silencing of the Rag2 gene in non-obese diabetic (NOD) mice. In embodiments of the invention, the animal is produced by introducing such genetic modifications in wild type animals.

In embodiments of the invention, an animal exhibits one or more (preferably, all) of the following pathological findings in the liver:
  (i) infiltration of inflammatory cells;
  (ii) accumulation of ASMA+ hepatic stellate cells associated with hepatic fibrosis; and
  (iii) fibrosis around in the portal area and the central vein.

Accordingly, embodiment of the invention, the animals may be structurally characterized by the above-described pathological morphologies (i)-(iii).

The animals of the invention may thus display inflammation and fibrosis particularly evident around portal tracts and central veins and accompanied with evidence of abnormal intrahepatic bile ducts. In examples described in more detail below, the extensive cellular infiltration was found to consist mainly of macrophages, granulocytes, particularly eosinophils, and mast cells. This inflammatory syndrome was mediated by a transgenic population of natural killer T cells (NKT) induced in an immunodeficient NOD genetic background. The disease is transferable to immunodeficient recipients, while polyclonal T cells from unaffected syngeneic donors can inhibit the disease phenotype.

Natural killer T (NKT) cells constitute a population of unconventional T lymphocytes that express the αβ T cell receptor (TCR) together with several NK surface markers and recognize glycolipids presented by the MHC class I like CD1d molecule (Bendelac, J Exp Med. 182(6):2091-6, 1995; Godfrey et al. Nat Immunol. 11(3):197-206, 2010). The NKT cell population is heterogeneous where the majority, referred to as type I NKT cells, express an invariant TCR and display specificity for glycolipids presented by CD1d, with the prototype antigen being α-GalCer. Type II NKT cells resemble type I NKT cells in their restriction to CD1d, but use a diverse set of TCR and have a less well-defined range of antigen specificities. NKT cells are highly enriched in the liver and have been shown to be able to promote as well as protect from inflammation and fibrosis development, suggesting that the net effect of the NKT cells depends on the balance between these properties (Chuang et al. Clin Liver Dis. 12(2):333-47, 2008; Ishikawa et al. J Hepatol. 54(6):1195-204, 2011; Park et al. Hepatology 49(5):1683-94, 2009; Takeda et al. Proc Natl Acad Sci USA. 97(10): 5498-503, 2000). In line with this activated NKT cells are known to be able to produce large amounts of both antifibrotic (e.g. interferon (IFN)-γ) and profibrotic (e.g. interleukin-4 (IL-4), IL-13) cytokines (Ishikawa et al. J Hepatol. 54(6):1195-204, 2011; Park et al. Hepatology. 49(5):1683-94, 2009; de Lalla et al. J Immunol 173(2):1417-25, 2004).

The animal according to embodiments of the invention may be defined as a transgenic animal. As used herein, "transgenic" is to be understood as referring to a specific desired genetic modification being introduced into the genome of the animal. A modification may be represented by the introduction of a gene or a part thereof, or the removal or silencing of a gene, or a modification that alters the expression of a gene. The origin of the modification (e.g., a newly introduced gene) may be the same species as the animal in question, or it may be a different species.

In embodiments of the present invention, a transgenic modification may comprise a TCRα gene and/or a TCRβ gene(s) introduced into an animal. In embodiments, a modification may also comprise a null mutation of the Rag-2 locus. The modification man be introduced into an animal that is an ancestor of an animal according to embodiments of the invention. Thus, a genetic modification is not necessarily introduced via molecular genetic engineering directly into the animals according to the invention, but may be introduced into an ancestor animal which is further bred using conventional methods to produce a descendant animal according to the invention having the desired genotype. In embodiments, the TCRα and/or the TCRβ gene(s) may originate from the same species. In embodiments where the animal of the invention is a mouse, the TCRα and/or the TCRβ gene(s) may be of murine origin.

The type of animals to be used in the present invention are not particularly limited, as long as they are useful as experimental animals. Such animals typically include non-human animals, typically non-human vertebrates, for instance non-human mammals, such as rodents. Examples of animals that can be used for producing model animals of the present invention specifically include mice, rats, rabbits, dogs, chickens, and monkeys (such animals are sometimes also referred to simply as "experimental animals"). The genetic background of the animals to be used to produce model animals of the present invention is not particularly limited; and it is possible to use animals with any genetic background. In general, wild-type animals can be preferably used.

The methods described herein stably produces animals that are capable of developing, at an early stage, pathological conditions similar to human fibrosis in the liver, kidney, and skin.

For example, to produce mice that develop pathological conditions similar to those of humans, fertilized oocytes from NOD mice were injected with constructs containing cDNA from a TCRα or TCRβ gene, respectively, to generate two single transgenic mice. The two mouse strains were bred together to generate a double transgenic mouse expressing the TCRα and TCRβ genes (Duarte et al. J Immunol 173:3112, 2004). The double transgenic mouse was the bred to a NOD.Rag2$^{-/-}$ mouse to introduce a null-mutated Rag-2 locus. This generated a mouse according to embodiments of the present invention, also referred to as the N-IF mouse.

As will be described in more detail in the Examples below, N-IF mice were sacrificed at different ages and organs (mainly liver, skin, kidney) were analyzed histopathologically (HE staining, immune staining for macrophages, NKT cells, hepatic stellate cells and fibroblasts) and immunohistochemically (hepatic stellate cells, bile ducts). The animals were also assessed for inflammation and fibrosis by the following methods:

- determination of the cellular composition of infiltrates of the affected organs using flow cytometry;
- determination of systemic and local production of pro-inflammatory and pro-fibrotic cytokines using the mouse Th1/Th2/Th17/Th22 13-plex (eBiosciences).
- determination of the hydroxyproline content in the affected organs using the Hydroxyproline Colorimetric Assay kit (BioVision);
- serum-biochemical tests using a fully automated Architect c4000 (Abbott Laboratories, Abbott Park, Ill., US);
- gene expression analysis using Real-Time RT-PCR.

The results showed extensive cellular infiltration in the N-IF mouse liver dominated by granulocytes, particularly eosinophils, macrophages, mast cells and multinucleated giant cells which could be observed already at 3 weeks of age. This effect was most pronounced in the portal tracts and central veins associated with abnormal intrahepatic bile ducts. The inflammation in the liver was accompanied by fibrosis primarily localized to the portal tracts and central veins and with varying degrees of periportal and bridging fibrosis with deposits of matrix proteins and accumulation of anti-smooth muscle actin (ASMA) expressing cells in the inflamed areas of the liver.

The cytokine profile of the N-IF mouse showed reduced levels of IFNγ and IL-2 and increased expression of IL-4 and IL-5, but also production of additional type 2 cytokines such as IL-13, and a dramatic increase in IL-6 production.

In embodiments, the animals of the present invention are characteristic in that the pathological conditions of renal fibrosis and skin fibrosis can be observed at the same time.

Furthermore, since the model animals of the present invention typically exhibit a pathological condition of inflammation and/or fibrosis that may occur spontaneously, and that does not recover spontaneously (although it may be reversible e.g. upon treatment), the animals of the invention can be suitably used in testing and assessing the efficacy of drugs directed to inflammatory conditions such as hepatic inflammation, hepatic inflammation, hepatic fibrosis, abnormal intrahepatic bile ducts, inflammation or fibrosis of the skin, renal inflammation, or renal fibrosis. The inflammation may be chronic inflammation. For example, animals of the present invention can be used in preclinical tests to screen for therapeutic agents, or to assess the efficacy of a candidate therapeutic agent. Thus, the animals of the invention are useful in developing agents.

Specifically, in embodiment the present invention provides methods of screening for substances for treating or preventing an inflammatory condition, especially chronic inflammation, or fibrosis, which comprise:

a) Administering a test substance to a model animal of the present invention; and
b) Evaluating an ameliorating effect on the inflammatory condition or fibrosis.

The inflammatory condition or fibrosis may be any one of the conditions mentioned herein. Specifically, the condition may be chronic hepatic inflammation and/or hepatic fibrosis.

The test substances to be used in these methods are not particularly limited. For example, such substances include single compounds such as natural compounds, synthetic compounds, organic compounds, inorganic compounds, proteins, and peptides, as well as compound libraries, expression products of gene libraries, cell extracts, cell culture supernatants, products of fermenting microorganisms, extracts of marine organisms, and plant extracts, but are not limited thereto.

Methods for administering test substances or medicinal substances of the present invention are not particularly limited; however, they can be administered, for example, by injection. When such a test substance is a protein, for example, a viral vector carrying a gene encoding the protein may be constructed and can be introduced into model animals of the present invention using their infectability.

In the step of (b), the ameliorating effect on fibrosis can be evaluated by assessing the pathological findings of the model animals. The pathological findings of fibrosis include, for example, the above-described pathological findings (pathological morphologies). Herein, "amelioration" means that the symptoms of fibrosis are alleviated or restored to normal. By using as an indicator the pathological findings described herein, those skilled in the art can appropriately evaluate whether the symptoms of hepatic fibrosis are ameliorated in the model animals.

For instance, as demonstrated in the below Examples, model animals according to embodiments of the present invention may exhibit increased hydroxyproline content relative to an organ of an animal unaffected by fibrosis, such as the asymptomatic 24αβNOD mouse (see FIG. 5). Hence, an ameliorating effect may be represented by a decrease of the level of hydroxyproline in an organ affected by fibrosis, relative to a level of hydroxyproline in said organ prior to administration of a test substance.

In embodiments of the invention, substances that produce the ameliorating effect in the step of (b) above can be selected as substances for treating or preventing hepatic fibrosis.

Furthermore, medicinal substances (therapeutic agents) can be assessed for their efficacy in ameliorating an inflammatory condition, such as chronic inflammation or fibrosis, by using model animals of the present invention. Specifically, the present invention provides methods for evaluating the efficacy of medicinal substances in ameliorating an inflammatory condition, such as chronic inflammation or fibrosis, which comprise the steps of:

a) Administering a test medicinal substance to a fibrosis model animal according to embodiments of the present invention; and
b) Evaluating an ameliorating effect on the inflammatory condition or fibrosis.

The inflammatory condition or fibrosis may be any one of the conditions mentioned herein. Specifically, the condition may be chronic hepatic inflammation and/or hepatic fibrosis.

The type of medicinal substances that can be evaluated for efficacy by the above-described methods is not particularly limited; and such medicinal substances include, for example, various known pharmaceutical agents (low-molecular-weight compounds, proteins, nucleic acids, and the like).

When a test medicinal substance exerts an ameliorating effect on hepatic fibrosis, as determined by observation of pathological findings as described above or by other methods of assessment of the degree or severity of inflammation/fibrosis appreciated by a person of skill in the art, the medicinal substance is judged to have therapeutic effect on hepatic fibrosis.

Furthermore, in embodiments of the invention, the animals are characterized in that they develop renal fibrosis simultaneously and in conjunction with hepatic fibrosis. Thus, animals of the present invention may be useful as model animals for renal fibrosis.

Thus, in further embodiments, the present invention provides non-human model animals of renal fibrosis. Accordingly, in analogy with what has been described above with regard to inflammatory conditions and/or fibrosis in general or specifically hepatic inflammation or fibrosis, animals according to embodiments of the invention may also be used in methods of screening for and developing agents suitable for treating or preventing renal fibrosis. For example, candidate therapeutic agents for treating or preventing renal fibrosis can be screened by administering test substances to a model animal according to embodiments of the invention, and by evaluating an ameliorating effect on renal fibrosis. Thus, a method of screening for a substance suitable for treating or preventing renal fibrosis, may comprise the steps of:

a) administering a test substance to a non-human animal according to embodiments of the present invention; and
b) evaluating an ameliorating effect on renal fibrosis.

Furthermore, in embodiments of the invention, the animals are characterized in that they develop inflammation and fibrosis of the skin simultaneously and in conjunction with hepatic fibrosis. Thus, model animals of the present invention may be useful as model animals for fibrosis of the skin.

Thus, in further embodiments, the present invention provides non-human model animals of skin fibrosis. Accordingly, in analogy with what has been described above with regard to inflammatory conditions and/or fibrosis in general or specifically hepatic inflammation or fibrosis, animals according to embodiments of the invention may also be used in methods of screening for and developing agents suitable for treating or preventing skin fibrosis. For example, candidate therapeutic agents for treating or preventing skin fibrosis can be screened by administering test substances to the animals according to embodiments of the invention, and by evaluating an ameliorating effect on skin fibrosis. Thus, a method of screening for a substance suitable for treating or preventing skin fibrosis, may comprise the steps of:

a) administering a test substance to a non-human animal according to embodiments of the present invention; and
b) evaluating an ameliorating effect on skin fibrosis.

The invention will be further illustrated by means of the following examples.

EXAMPLES

Herein below, the present invention will be described more specifically with reference to the Examples, but it is not limited thereto.

(a) Preparation of Fibrosis Model Mice

TCRαβ-transgenic mice were made directly on a NOD genetic background using TCR expression constructs encoding a CD1d-reactive TCR. Each TCR chain construct (containing rearranged TCR Vα3.2 and TCR Vβ9 regions, respectively) was microinjected alone to create single chain transgenic mice. Transgenic founders were screened by flow cytometry for transgene expression Mice positive for the transgenic TCRα and β chains were intercrossed to obtain TCRαβNOD mice expressing the complete transgenic TCR.

The fibrosis model mouse was generated by crossing the TCRαβNOD and the NOD.Rag2$^{-/-}$ mouse strains. Crossing the TCRαβNOD mouse with the B6.Rag2$^{-/-}$ mouse strains and then backcrossing to NOD for 10 generations generated the TCRαβB6.Rag2$^{-/-}$ fibrotic model mice.

For evaluation the mice were sacrificed by cervical dislocation.

(b) Histological Assessment

Liver, skin or kidney tissue were fixed in 4% neutral buffered formalin, embedded in paraffin and sectioned. Sections (5 μm) were stained with hematoxylin and eosin (H&E), Toluidine blue (TolB) or Sirius red and were evaluated microscopically. Immunohistochemical staining was performed on liver biopsies fixed in 4% paraformaldehyde and embedded in OCT. The frozen tissues were cut in 5 μm thick sections and stained using primary antibody against cytokeratin 7 (1:1500, Abcam, EPR17078), F4/80 (1:200, AbD Serotec, CI:A3-1), CD3 (1:200, Sigma C7930), Collagen I (1:200, Abcam, ab21286) CD45 (1:200, eBioscience, 30-F11), matrix metallopeptidase 9 (MMP9) (1:300, Abcam, ab38898) and anti-smooth muscle actin (ASMA) (1:100, Abcam, ab5694) and secondary anti-rabbit (1:2000, Alexa 594), anti-rat (1:2000, Alexa 647) antibodies. The nuclei were visualized with DAPI. The sections where analyzed using confocal microscopy.

Hepatomegaly was observed in animal model mice of the present invention with a 100% penetrance. This was evidenced from the increasing liver weight (LW) to body weight (BW) ratio of the N-IF mice compared to controls (FIG. 1).

Figure 2:
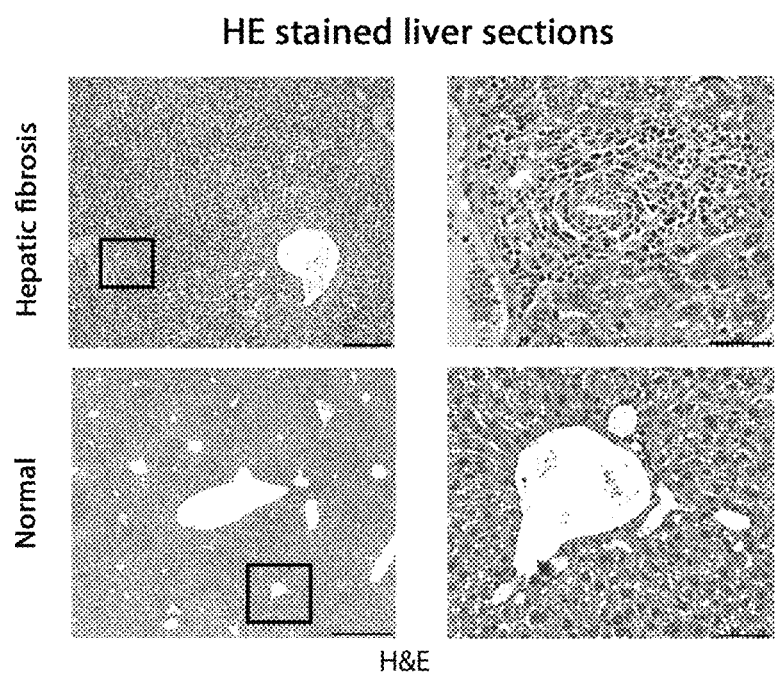
FIG. 2 shows in photographs the result of HE staining of hepatic tissue from a 8-week-old fibrotic N-IF mouse according to embodiments of the present invention (top) and from an age-matched C57BL/6J mouse serving as control (bottom). Scale bars are 500 µm in the overview photographs (left) and 100 µm in the further enlarged photographs (right).

Histologically extensive cellular infiltration was observed, dominated by granulocytes, particularly eosinophils, macrophages, mast cells and multinucleated giant cells, which could be observed already at 3 weeks of age. In addition, scattered megakaryocytes and hepatic extramedullary hematopoiesis with colonies of myelopoiesis showing both neutrophilic and eosiniphilic differentiation was observed in the N-IF mouse liver. The granulomatous inflammation in the N-IF mouse was most pronounced in the portal tracts and central veins associated with abnormal intrahepatic bile ducts (FIG. 2).

Figure 3:
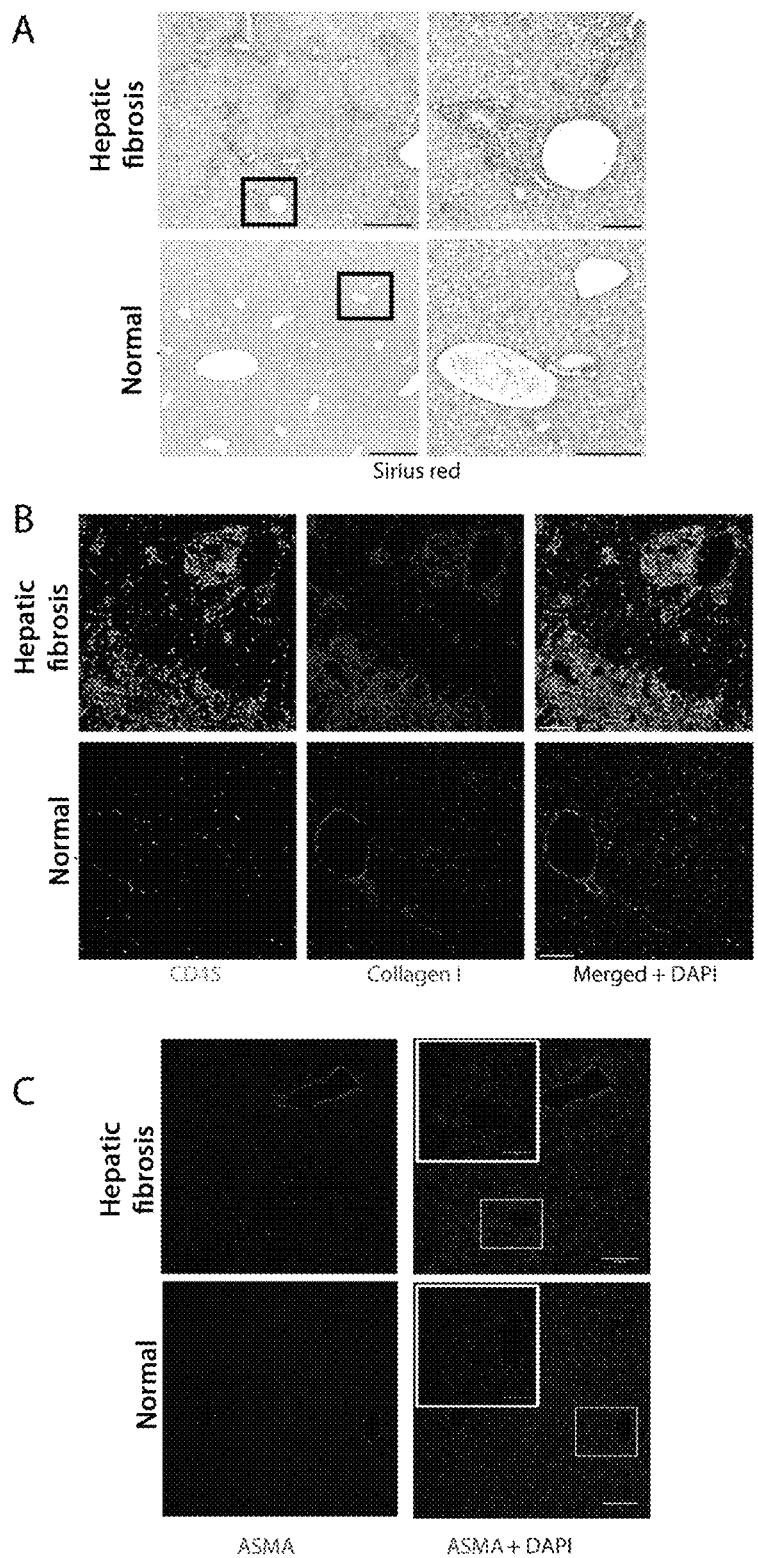
FIG. 3 shows in photographs results of immunostaining of hepatic tissue from a fibrotic mouse according to embodiments of the present invention and of a normal control mouse. (A) shows sirius red staining, (B) shows immunostaining using anti-CD45, anti-collagen and DAPI staining; and (C) shows immunostaining using ASMA and DAPI.

The inflammation in the liver was accompanied by fibrosis primarily localized to the portal tracts and central veins and with varying degrees of periportal and bridging fibrosis with deposits of matrix proteins such as collagen I together with accumulation of anti-smooth muscle actin (ASMA) expressing cells were observed in the inflamed areas of the N-IF mouse liver (FIG. 3).

I-(c) Serum and Tissue Biochemical Analyses

Serum was collected by centrifugation of clotted whole blood for 10 minutes at 1500×g. The cleared supernatant was collected and AST, ALT, ALP, total bilirubin and bile acid was measured using a fully automated Architect c4000 (Abbott Laboratories, Abbott Park, Ill., US). The liver hydroxyproline content was determined with the Hydroxyproline Colorimetric Assay kit (BioVision). An increase in the serum levels of bile acid in the N-IF mouse compared to control strains was observed (FIG. 4) suggesting that the N-IF mouse developed cholestasis, but no increase in serum bilirubin or in alkaline phosphatase was detected.

Figure 5:
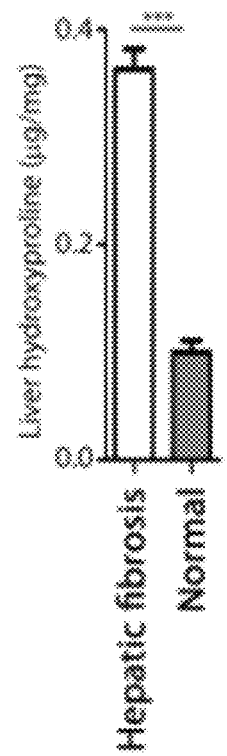
FIG. 5 is a graph showing results of hepatic tissue-biochemical test of hydroxyproline in fibrotic mice ("hepatic fibrosis") according to embodiments of the present invention compared with control mice ("normal").

The development of fibrosis was also biochemically confirmed by the significant increase in the level of hydroxyproline in livers from N-IF mice compared to asymptomatic 24αβNOD trangenic mice (FIG. 5; "normal" represents the 24αβNOD mouse and "hepatic fibrosis" represents the N-IF mouse).

I-(d) Analysis of Cellular Composition

Liver leukocytes were obtained by incubating cut pieces of liver in 1.0 mg/ml collagenase II solution (Sigma) for 40 min at 37° C., after which the tissue was minced through a 70 μm mesh and leukocytes were separated on a 50/25 Percoll (GE Healthcare) by centrifugation. Cells were stained in FACS buffer (3% FCS in PBS). Prior to surface staining the cells were incubated with the 2.4G2 (anti-CD16/

CD32) Ab (BD Biosciences), to prevent unspecific binding. The cells were then incubated with fluorochrome-conjugated anti-murine antibodies specific for the following cell surface markers: CD45 (30-F11) and Ly6G (1A8) from Biolegend, CD11 b (M1/70), Vα3.2 (RR3-16) and V139 (MR10-2) from eBioscience and Siglec-F (E50-2440) from BD Bioscience. Cell viability was determined using fixable viability dye (eBioscience). The stained cells were analyzed using a BD LSR II flow cytometer and Kaluza software (Beckman Coulter).

Figure 6:
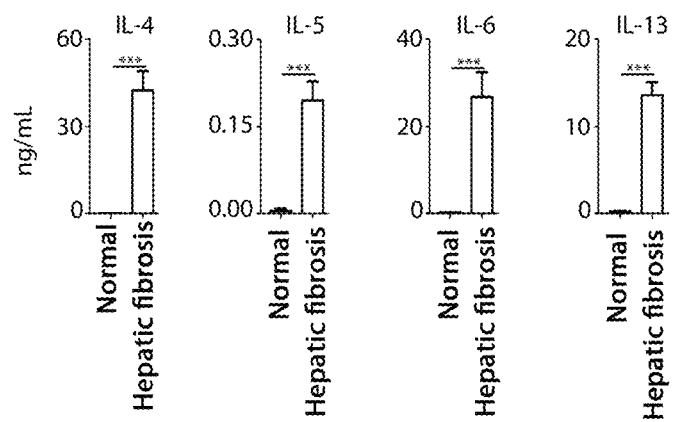
FIG. 6 shows graphs illustrating results of the biochemical analysis of cytokines IL-4, IL-5, IL-6 and IL-13 after anti-CD3 stimulation in vitro of total (A) spleen leukocytes, or (B) liver leukocytes, respectively, from mice according to embodiments of the present invention ("hepatic fibrosis") compared with control mice ("normal").
Figure 6:
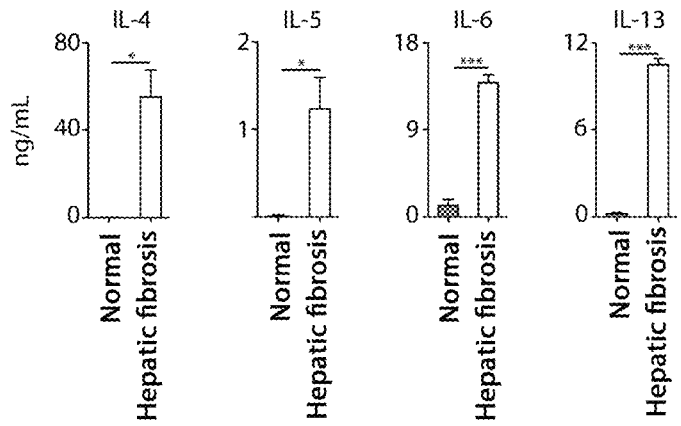

The systemic cytokine profile of the spleen cells of the hepatic fibrosis model mice displayed an increased expression of IL-4 and IL-5 but also production of additional type 2 cytokines like IL-13 as well as a dramatic increase in IL-6 production. Similar to the systemic representation of cytokines in the model mice, the cytokine profile in total liver leukocytes displayed high levels of IL-6 together with the cytokines IL-4, IL-5 and IL-13 as well as of the cytokines IFNγ and IL-2 (FIG. 6).

I-e) Cell Activation and Cytokine Analysis.

Single-cell suspensions from spleen were prepared by disrupting the tissue through a 70 μm mesh. Total splenocytes ($2 \times 10^6$) and liver leukocytes ($2 \times 10^5$) were activated using anti-CD3 Ab ($4_4$/ml, clone 154-2C11, BD Biosciences). In all cases cells were grown in complete medium (RPMI 1640 medium supplemented with 10% FCS, 100 U/mL penicillin/streptomycin, 2.5% sodium bicarbonate (7.5% solution), 1 mM sodium pyruvate and 69 μM 1-thioglycerol). The supernatants were collected after 24 h and analyzed for cytokines using the mouse Th1/Th2/Th17/Th22 13-plex (eBiosciences) according to manufacturer's instructions.

The systemic cytokine profile of the N-IF mice was altered with significantly increased expression of IL-4 and IL-5 but also increased production of additional type 2 cytokines like IL-13 compared with control mice. In addition, observed a dramatic increase in IL-6 production was observed in the N-IF mice. Similar to the systemic representation of cytokines, the cytokine profile in total liver leukocytes from N-IF mice displayed high levels of IL-6 together with the cytokines IL-4, IL-5 and IL-13 (FIG. 6).

Discussion

The N-IF mouse presented herein spontaneously develops liver inflammation and fibrosis associated with abnormal intrahepatic bile ducts. The development of fibrosis in this model is preceded by a state of chronic inflammation reflecting an important aspect characteristic of many human fibrotic disorders. Furthermore, the N-IF mouse provides several previously unmet demands on an animal model for fibrosis e.g. in terms of reproducibility and spontaneous onset compared with most presently available animal models for fibrosis. The N-IF mouse was originally generated to investigate the role of type II NKT cells as regulators of the autoimmune diabetes developing in the NOD mouse. It was previously reported that transgenic expression of the 24αβTCR resulted in the production of type II NKT cells, efficiently inhibiting the development of diabetes in the NOD mouse (Duarte et al. J Immunol 173:3112, 2004; Kadri et al. J Immunol 188(7):3138-49, 2012). In view of this finding, it completely was unexpected that expression of the same transgenic TCR in an immunodeficient NOD.Rag2$^{-/-}$ genetic background resulted in the development of progressive inflammation and fibrosis in multiple organs.

Figure 4:
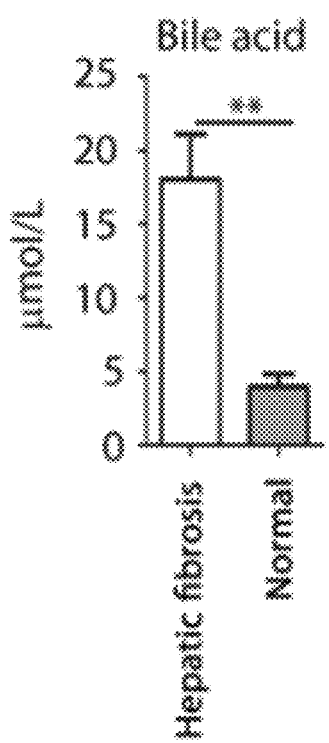
FIG. 4 is a graph showing results of serum-biochemical test of bile acid content in fibrotic mice ("hepatic fibrosis") according to embodiments of the present invention and of with control mice ("normal").

To elucidate the mechanisms underlying this process adoptive transfer experiments were carried out, demonstrating that splenocytes from the N-IF mouse could induce inflammation in naïve NOD.Rag2$^{-/-}$ recipients while splenocytes depleted from transgenic NKT cells could not (FIG. 4). Thus, the pathology of the N-IF mouse was driven by the transgenic NKT cells expressing a type II NKT cell TCR made up by the Vα3.2 and the V139 TCR chains. Further, the failure to develop the inflammatory and fibrotic liver disease of the single transgenic 24αNOD.Rag2$^{-/-}$ and 24βNOD.Rag2$^{-/-}$ mice suggested that the formation of a complete TCR and thus the generation of a functional NKT cell population may be required for the disease to develop.

While the full understanding of the underlying molecular mechanisms still remains to be elucidated, it has been noted that the monoclonal population of transgene expressing NKT cells of the N-IF mouse shifted from the predominant expression of IFNγ and IL-2 in the 24αβNOD mice to a mixed type 1/type 2 cytokine pattern with high expression also of IL-4, IL-5, IL-13 and IL-6. This cytokine profile is likely to underlie the activation and recruitment of inflammatory cells including neutrophils, eosinophils and mast cells to the liver. Further, the observed matrix deposition and accumulation of ASMA positive cells in the inflamed areas of the liver, together with the unaltered AST/ALT ratio, is in line with the notion of a crosstalk between the transgenic NKT cells and hepatic stellate cells as a major mechanism leading to the development of extensive periportal and bridging fibrosis in the N-IF mouse.

The two major subsets of NKT cells, type I and type II, have been assigned opposing roles in chronic liver disease (Bandyopadhyay et al. Cell Mol Immunol 13(3):337-46, 2016; Bendelac et al. Annu Rev Immunol 25:297-336, 2007) where Type I NKT cells have been reported to have mainly a proinflammatory role while Type II NKT cells have been suggested to have a potentially regulating role (Kumar and Delovitch, Immunology 142(3):321-36, 2014). In this scenario, the pro-inflammatory and pro-fibrotic properties of the transgenic NKT cell population of the N-IF mouse may be counterintuitive, given that the transgenic TCR was derived from a type II NKT cell (Duarte et al. J Immunol. 173(5):3112-8, 2004).

The fact that the N-IF transgenic NKT cells express a mixed Th1/Th2 cytokine profile may provide a clue to their disease promoting effect. The disease phenotype of the N-IF mouse can efficiently be inhibited by a functional adaptive immune system as exemplified by the absence of inflammation and fibrosis in the 24αβNOD transgenic mouse. Under these conditions, the transgene-expressing NKT cell population as well as the systemic cytokine profile is dominated by IFNγ rather than type 2 cytokines. It is interesting to note that despite the reduction in inflammation resulting from the transfer of NOD T cells, as well as the restoration of the expression levels of most pro-inflammatory cytokines, no obvious reduction in IL-4 production was observed. This suggests that at this stage of the disease process, IL-4 cannot be the main driving force of the inflammation. The fact that T cells from wild type NOD mice could, at least in part, revert the type 2 biased cytokine profile suggests that this shift is controlled by a so far unidentified T cell component (s). Regulatory T cells (Treg) have a critical role in regulating immune mediated liver disease (Liberal et al. IUBMB Life. 67(2):88-97, 2015). Thus, Treg cells constitute a plausible candidate for mediating the observed control of the N-IF mouse phenotype.

The failure of 24αβB6.Rag2$^{-/-}$ mice to develop disease demonstrated that the NOD mouse contained disease promoting genetic factors(s). Moreover the genetic crossing of the N-IF mouse to B6.Rag2$^{-/-}$ mice to generate F1(24αβNOD.Rag2$^{-/-}$×B6.Rag2$^{-/-}$) mice expressing the 24αβTCR revealed that the NOD gene(s) promoting the disease development were dominant.

The fibrosis observed in the portal tracts of the N-IF mouse is of particular interest since it is typical of human PBC but not represented in most other models of the disease (Chuang et al. Clin Liver Dis. 12(2):333-47, 2008; Wang et al. Semin Liver Dis. 34(3):285-96, 2014).

In conclusion, the present invention provides new animal models of fibrotic disease, which develop hepatic fibrosis as well as renal and/or dermal fibrosis. The use of such model animals facilitates the analysis of the pathogenesis and the pathological condition of human hepatic fibrosis, and facilitates the development of techniques and agents for treating human hepatic fibrosis, as well as renal and/or dermal fibrosis.

Variations to the disclosed embodiments can be understood and effected by the skilled person in practicing the claimed invention, from a study of the drawings, the disclosure, and the appended claims. In the claims, the indefinite article "a" or "an" does not exclude a plurality. References to the plural includes the singular, unless specifically stated otherwise. Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereof.

All references cited herein are incorporated by reference to the extent allowed.

The invention claimed is:

1. A non-obese diabetic (NOD) mouse comprising in its genome a genetic construct comprising exogenous CD1d-reactive T cell receptor (TCR)α and TCRβ genes and a null mutated Rag-2 locus, wherein the mouse expresses exogenous CD1d-reactive TCRα and TCRβ, and wherein the mouse spontaneously develops chronic inflammation and fibrosis.

2. The mouse according to claim 1, wherein the mouse exhibits one or more of hepatic inflammation, hepatic fibrosis, abnormal intrahepatic bile ducts, inflammation or fibrosis of the skin, renal inflammation, and renal fibrosis.

3. A method of making a genetically modified mouse comprising the steps of:
   a) providing fertilized first and second oocytes from a NOD mouse;
   b) introducing a first genetic construct comprising cDNA of a CD1d-reactive TCRα gene into said first oocyte and introducing a second genetic construct comprising cDNA of a CD1d-reactive TCRβ gene into said second oocyte;
   c) implanting said first and second oocytes in one or more surrogate mice, to generate at least to two single transgenic mice;
   d) breeding said at least two mice together to generate a double transgenic mouse expressing the TCRα and the TCRβ genes;
   e) breeding said double transgenic mouse with a NOD.Rag2$^{-/-}$ mouse to introduce a null-mutated Rag-2 locus into said double transgenic mouse.

4. A method of screening for an agent suitable for prevention or treatment of chronic inflammation and/or fibrosis, comprising the steps of
   a) administering a test agent to the mouse of claim 1, wherein said animal or mouse exhibits inflammation and/or fibrosis, and
   b) evaluating an ameliorating effect on the inflammation and/or fibrosis.

5. A method of evaluating the efficiency of a therapeutic agent for treatment of inflammation or fibrosis, comprising the steps of
   a) administering a test agent to the mouse of claim 1, wherein said animal or mouse exhibits inflammation and/or fibrosis, and
   b) evaluating an ameliorating effect on the inflammation and/or fibrosis.

6. The method according to claim 4, wherein the inflammation and/or fibrosis is selected from the group consisting of hepatic inflammation, hepatic fibrosis, inflammation or fibrosis of the skin, renal inflammation, and renal fibrosis.

7. The method according to claim 6, wherein the inflammation is chronic inflammation.

8. The method according to claim 4, wherein an ameliorating effect is represented by one or more of: reduced fibrosis, reduced inflammation, and return to a normal morphology.

9. The method according to claim 4, wherein an ameliorating effect is represented by a reduction of systemic or local production of one or more pro-inflammatory or pro-fibrotic factor(s) or marker(s) of inflammation and/or fibrosis and the step b) comprises determining a level of at least one pro-inflammatory or pro-fibrotic factor in a sample obtained from said mouse after said step a) of administering, and optionally comparing said level with an initial level of said pro-inflammatory or pro-fibrotic factor(s) or marker(s) determined in an initial sample obtained from said mouse prior to said step a) of administering.

10. The method according to claim 4, wherein an ameliorating effect is represented by a decreased level of hydroxyproline in an organ affected by fibrosis relative to a level of hydroxyproline in said organ prior to said administration, and step b) comprises determining the level of hydroxyproline in an affected organ.

* * * * *